(12) United States Patent  
Nakanishi

(10) Patent No.: US 6,607,384 B1
(45) Date of Patent: Aug. 19, 2003

(54) LIGHTING DEVICE FOR DENTAL OR MEDICAL INSTRUMENT, AND DENTAL OR MEDICAL INSTRUMENT HAVING LIGHTING DEVICE

(75) Inventor: Kensuke Nakanishi, Kanuma (JP)

(73) Assignee: Nakanishi Inc., Tochigi (JP)

( * ) Notice: Subject to any disclaimer, the term of this patent is extended or adjusted under 35 U.S.C. 154(b) by 0 days.

(21) Appl. No.: 09/691,998

(22) Filed: Oct. 19, 2000

(30) Foreign Application Priority Data

Oct. 20, 1999 (JP) ............................................ 11-297899

(51) Int. Cl.[7] .................................................. A61C 3/00
(52) U.S. Cl. ......................................... 433/29; 433/114
(58) Field of Search ..................................... 433/29, 114

(56) References Cited

U.S. PATENT DOCUMENTS

| | | | | |
|---|---|---|---|---|
| 3,109,238 A | * | 11/1963 | Marks | 433/131 |
| 3,590,232 A | * | 6/1971 | Sadowski | 433/29 |
| 6,030,210 A | * | 2/2000 | Bianchetti | 433/29 |

FOREIGN PATENT DOCUMENTS

| | | | | |
|---|---|---|---|---|
| DE | 1466959 | * | 2/1969 | 433/29 |
| JP | 58-168311 | | 11/1983 | |
| JP | 7-275273 | | 10/1995 | |
| JP | 10-337292 | | 12/1998 | |
| JP | 11-104147 | | 4/1999 | |
| JP | 11-202164 | | 7/1999 | |

* cited by examiner

Primary Examiner—John J. Wilson
(74) Attorney, Agent, or Firm—Reed Smith Crosby Heafey LLP

(57) ABSTRACT

Disclosed is a lighting device for use with a dental or medical instrument having a tool in the distal part of the instrument for treatment of a site. The lighting device includes a plurality of LEDs and an LED holder encasing the plurality of LEDs and capable of being mounted on a distal part of the instrument. The LEDs are arranged so as to illuminate the site substantially without casting a shadow on the site in treatment when the LED holder is mounted on the instrument. Also disclosed is a dental or medical instrument including a tool in the distal part of the instrument for treatment of a site and a lighting device. The lighting device further includes a plurality of LEDs and an LED holder encasing the LEDs and provided in the distal part of the instrument. The LEDs are arranged so as to illuminate the site substantially without casting a shadow on the site in treatment.

17 Claims, 8 Drawing Sheets

LIGHTING DEVICE FOR DENTAL OR MEDICAL INSTRUMENT, AND DENTAL OR MEDICAL INSTRUMENT HAVING LIGHTING DEVICE

FIELD OF THE INVENTION

The present invention relates to a lighting device that is capable of being mounted on a dental or medical instrument for illuminating a treatment site. The present invention also relates to a dental or medical instrument having a lighting device for illuminating a treatment site.

BACKGROUND OF THE INVENTION

Recent dental or medical instruments, such as handpieces of a straight or contra-angle type, are often provided with a lighting device for illuminating a treatment site. Such lighting device is integrated in a treatment unit, and is designed to guide light from a light source to the head of a handpiece through an optical fiber. The light guided through the optical fiber is then emitted from the distal end of the fiber located in the head to illuminate a treatment site.

In such a conventional lighting device for dental or medical instruments using an optical fiber for guiding the light from the light source, however, an optical fiber having a core made of a quartz material or a multi-component glass is often used, which is difficult to bend and dispose in a handpiece, in particular, of a contra-angle type. Such an optical fiber is also prone to cracks to cause serious attenuation of light, becoming unserviceable. An optical fiber having a core made of a polymer material (plastic material) is also used, which cannot withstand repeated autoclaving.

The light introduced into the optical fiber is usually a visible light, a white light, or light from a halogen lamp. However, use of such lights is disadvantageous since a light source of such lights is expensive.

DISCLOSURE OF THE INVENTION

The present invention aims to solve these problems in the conventional lighting devices. It is therefore an object of the present invention to provide a lighting device that is capable of illuminating a treatment site substantially without casting a shadow on the treatment site, while the energy consumption and the cost are minimized.

It is another object of the present invention to provide a lighting device that is easy to mount even on a dental or medical instrument of an angled type such as a contra-angle handpiece.

It is another object of the present invention to provide a lighting device that can withstand repeated autoclaving.

It is still another object of the present invention to provide a dental or medical instrument having a lighting device that is capable of illuminating a treatment site substantially without casting a shadow on the site, while the energy consumption and the cost are minimized.

It is yet another object of the present invention to provide a dental or medical instrument having a lighting device that can withstand repeated autoclaving.

It is yet another object of the present invention to provide a dental or medical instrument having a lighting device that is easy to exchange when it is damaged.

According to the present invention, there is provided a lighting device for use with a dental or medical instrument having a tool in a distal part of said instrument for treatment of a site, said lighting device comprising:

a plurality of light emitting diodes, and an LED holder encasing said plurality of light emitting diodes and capable of being mounted on a distal part of said instrument, wherein said plurality of light emitting diodes are arranged so as to illuminate said site substantially without casting a shadow on said site in treatment when said LED holder is mounted on said instrument.

According to the present invention, there is also provided a dental or medical instrument comprising:

a tool in a distal part of said instrument for treatment of a site, and a lighting device comprising:

a plurality of light emitting diodes, and an LED holder encasing said plurality of light emitting diodes and provided in said distal part of said instrument, wherein said plurality of light emitting diodes are arranged so as to illuminate said site substantially without casting a shadow on said site in treatment.

PREFERRED EMBODIMENT OF THE INVENTION

The present invention will now be explained with reference to preferred embodiments of the invention, taken in conjunction with attached drawings.

Figure 1:
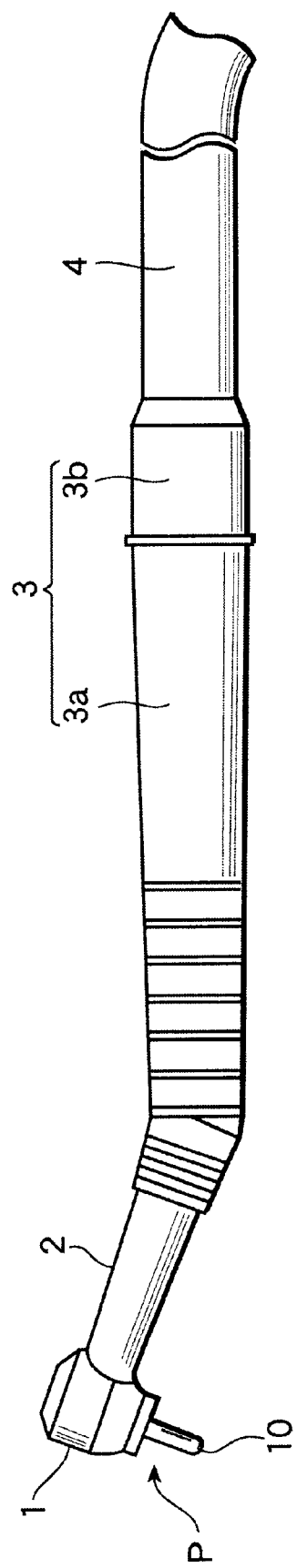
FIG. 1 is a side view of an embodiment of a dental or medical instrument having a lighting device according to the present invention.

FIG. 1 shows one embodiment of a handpiece of a contra-angle type having a lighting device according to the present invention. The handpiece includes a tool head 1 holding a treatment tool 10, a neck 2 extending from the head 1, a grip 3 detachably connected to the neck 2, and a flexible hose 4 connected to the proximal end of the grip 3. The head 1, neck 2, grip 3, and hose 4 are assembled in series. The grip 3 includes two detachable portions; a distal portion 3a and a proximal portion 3b. Piping and wiring for compressed air, cooling water, cleaning water, lighting device, and others extending through each of the distal and proximal portions 3a and 3b are connected to each other in an air- and water-tight manner via sealing pipes disposed at respective ends of the portions 3a and 3b. Since the structure of the handpiece except for the lighting device to be discussed later may be conventional, it is not discussed any further.

Figure 2:
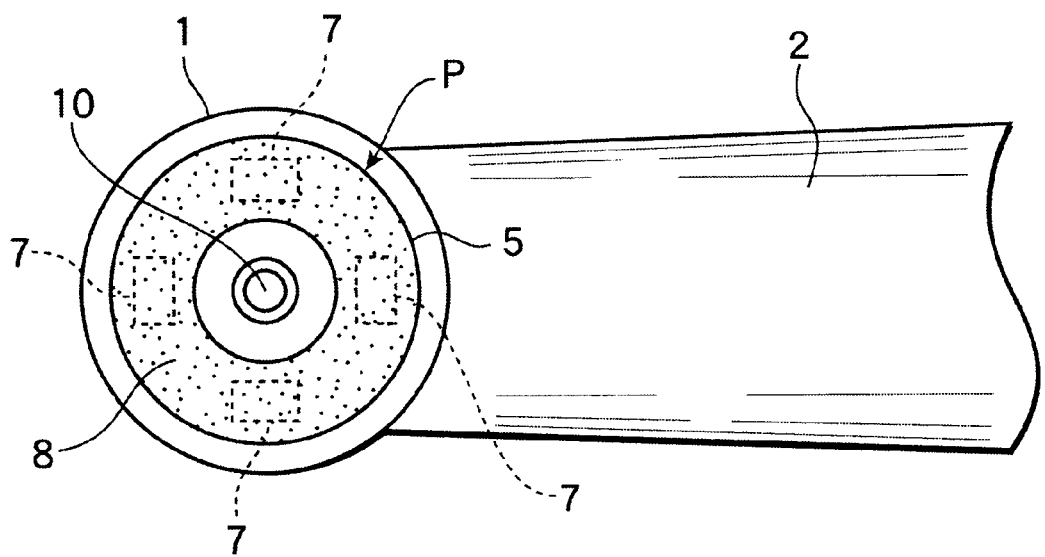
FIG. 2 is a partial enlarged bottom view of the tool head of the instrument of FIG. 1, showing one embodiment of a lighting device of the present invention.

The tool head 1 has on its lower side (tool attachment side) a lighting device P for illuminating around the tip of the tool 10, in other words, for illuminating a treatment site, substantially without casting a shadow on the site in treatment. FIG. 2 shows the details of this lighting device P having a plurality of light emitting diodes (LEDs) 7 and an LED holder 5. The LEDs 7 are encased in an LED holder 5 in the form of an annular groove provided integrally in the lower side of the head 1, and arranged substantially annularly around the tool 10 so as to illuminate the treatment site substantially without casting a shadow on the site in treatment.

In this embodiment, four LEDs 7 are arranged at regular 90° intervals. However, the number of LEDs are not particularly limited as long as a plurality of LEDs are used and as long as the LEDs can illuminate the treatment site substantially without casting a shadow on the site. The arrangement of the LEDs is not particularly limited, but preferably arranged at regular intervals.

The LEDs 7 are connected in series, in parallel, or in series-parallel connection to each other, and also connected to lead wires (not shown) extending through the grip 3 for being supplied with electric power by a treatment unit and the like power supply via the lead wires.

The LEDs 7, when supplied with electric power via the lead wires, illuminate around the tip of the tool 10 over a range as wide as 360°, thus illuminating the treatment site substantially without casting a shadow in treatment. Since flexible lead wires are used for connecting the LEDs 7 to the power supply, wiring in the vicinity of the tool head of even a contra-angle handpiece is facilitated without any problems of cracking of optical fibers or resulting attenuation of light, which often occur in conventional handpieces with an optical fiber. Further, since LEDs 7 consume less electric power than conventional light sources such as a halogen lamp, a smaller and inexpensive power supply may be employed, reducing the cost of the total system.

Preferably, the LEDs 7 are covered with a transparent, heat resistant synthetic resin 8 as shown in FIG. 2 so as not to be exposed to atmosphere. With such design, the lighting device P can withstand repeated sterilization with an autoclave without the LEDs 7 being damaged by the heat experienced during autoclaving.

Figure 3:
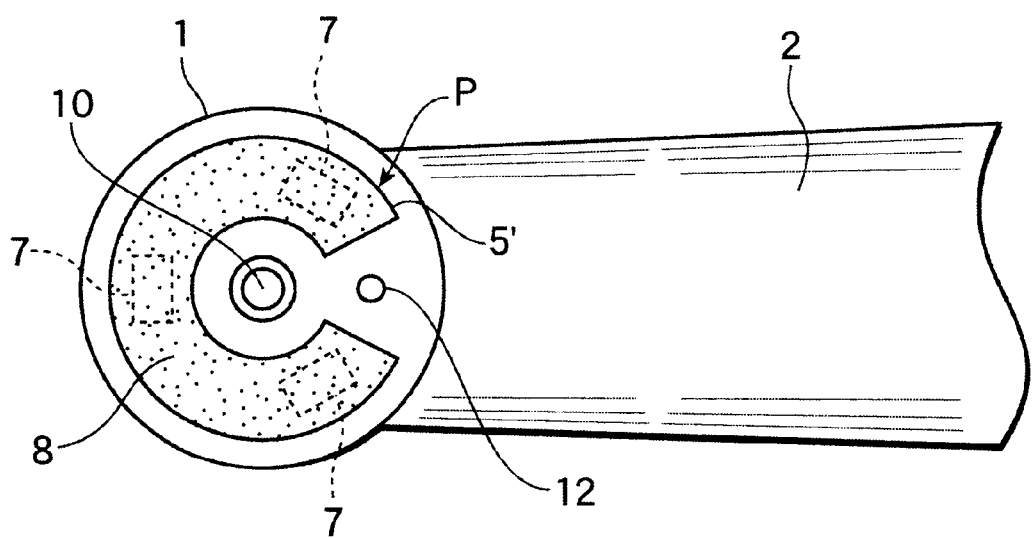
FIG. 3 is a partial enlarged bottom view similar to FIG. 2, showing another embodiment of a lighting device of the present invention.

FIG. 3 shows another embodiment of the lighting device of the present invention. In this embodiment, a lighting device P' similar to the lighting device P, has LEDs 7 encased in an LED holder 5' in the form of a horseshoe groove provided integrally in the lower side of the head 1, and arranged substantially in a horseshoe shape around the tool 10 so as to illuminate the treatment site substantially without casting a shadow on the site in treatment. In this embodiment, three LEDs 7 are arranged at regular 120° intervals.

This horseshoe LED holder 5' is particularly preferred when the handpiece has on the lower side of the head 1 near the tool 10 an orifice 12 for injecting compressed air, water, and the like. In this case, the lighting device P' is disposed so that the orifice 12 is placed between the ends of the horseshoe LED holder 5', allowing injection of chip air, washing water, or the like through the orifice 12 toward the treatment site.

The LEDs 7 in the holder 5' may also be covered with a transparent, heat resistant synthetic resin 8 as in the embodiment of FIG. 2.

Though the LED holders 5 and 5' have been described as being integrally formed in the head 1, the LED holder may alternatively be formed as an independent member separate from the head, and mounted on the lower side of the head either fixedly or detachably in a suitable manner. Further, a separate LED holder may be embedded in the annular or horseshoe groove provided in the head 1. The LED holder may be in any form and provided in any manner as long as the LEDs 7 are disposed so as to illuminate the treatment site substantially without casting a shadow on the site in treatment.

FIGS. 4 to 7 show yet another embodiment of the present invention. In this embodiment, a lighting device Q has an LED holder 50 and a clip 60 formed integrally with the holder 50, and is detachably mounted on a handpiece.

Figure 5:
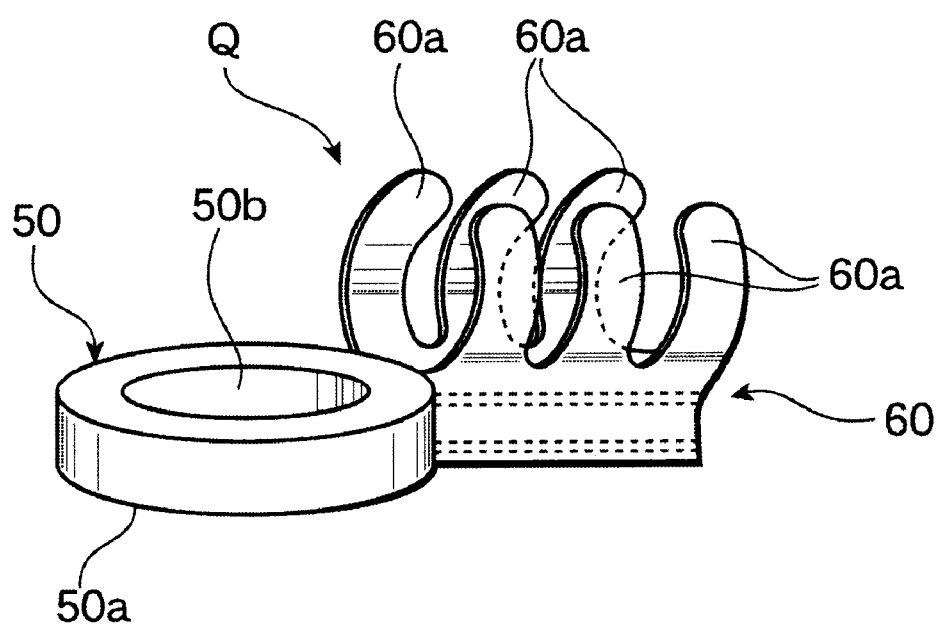
FIG. 5 is an enlarged perspective view of the lighting device of FIG. 4.
Figure 6:
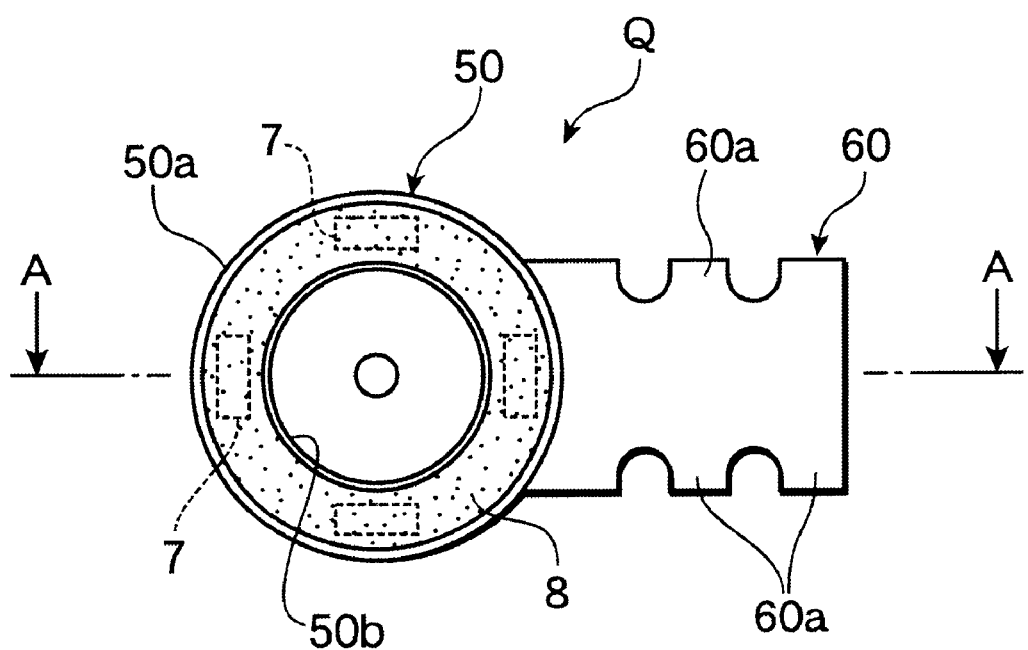
FIG. 6 is a bottom view of the lighting device of FIG. 5.
Figure 7:
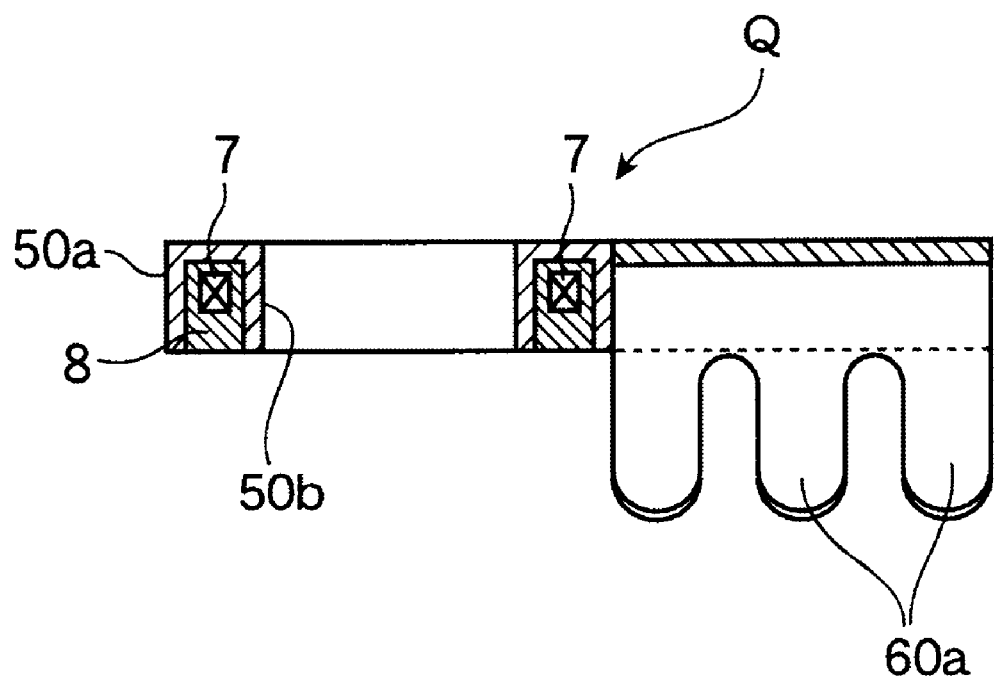
FIG. 7 is a sectional view taken along line A—A in FIG. 6.

Referring to FIG. 5, the LED holder 50 is in the form of a thin annular container 50a having a through hole 50b in the center thereof, and the LEDs 7 are arranged in the holder 50 at regular 90° intervals as shown in FIG. 6. The LED holder 50 may be filled with a transparent, heat resistant synthetic resin 8 as shown in FIG. 7. This resin 8 covers the LEDs 7 so as not to expose the LEDs 7 to atmosphere.

Figure 4:
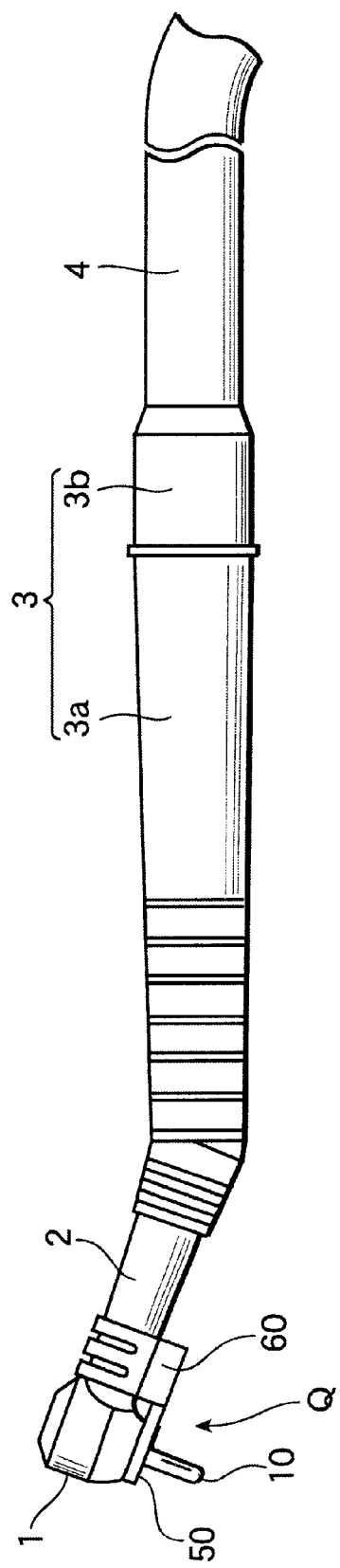
FIG. 4 is a side view of another embodiment of a dental or medical instrument having a lighting device according to the present invention.

The clip 60 has a plurality of pairs of gripping pieces 60a, and may be made of a resilient material such as metals or plastics. The clip 60 detachably engages with the handpiece near a transition portion between the head 1 and the neck 2 as shown in FIG. 4.

In this embodiment, though the clip 60 is formed integrally with the holder 50, the clip 60 may be formed as a separate part and attached to the holder 60 in a suitable manner.

In use, the LED holder 50 is placed on the lower side of the head 1 with the tool 10 of the handpiece penetrating through the hole 50b. The clip 60 engages with the transition portion between the head 1 and the neck 2 to hold the LED holder 50 in place with respect to the head 1. With this arrangement, the LEDs 7 are disposed substantially around the tool 10 to illuminate the treatment site over a range as wide as 360° substantially without casting a shadow on the site in treatment.

The plurality of LEDs 7 are connected either in series, in parallel, or in series-parallel connection, and usually two lead wires or terminals extend out of the LED holder 50, which wires or terminals are connected to a control power supply in the treatment unit via connecting means, such as lead wires, a flexible substrate, connectors, and others. At least a part of such connecting means may pass through the neck 2, grip 3, and flexible hose 4 so as to improve the appearance of the handpiece. It is preferred that the LEDs 7 are supplied with electric power via two driving lines.

The lead wires or terminals on the side of the LEDs 7 may be connected to lead wires or terminals on the side of the control power supply preferably via connectors. More specifically, the LED holder 50 is preferably provided with connector pins fixed to the lead wires or terminals from the LEDs 7, while the connector on the side of the power supply is preferably provided with a socket for receiving the connector pins. Using such connectors, the LED holder 50 may be easily detached from or mounted on the head 1, so that exchange or sterilization of the LED holder 50 may be facilitated.

For facilitating appropriate orientation of the connectors to match the polarity of the lead wires or terminals on the two connectors, it is preferred that the connectors have complementary concave-convex shapes, or that the wires or terminals on the connectors are not arranged in point symmetrical positions.

Figure 8:
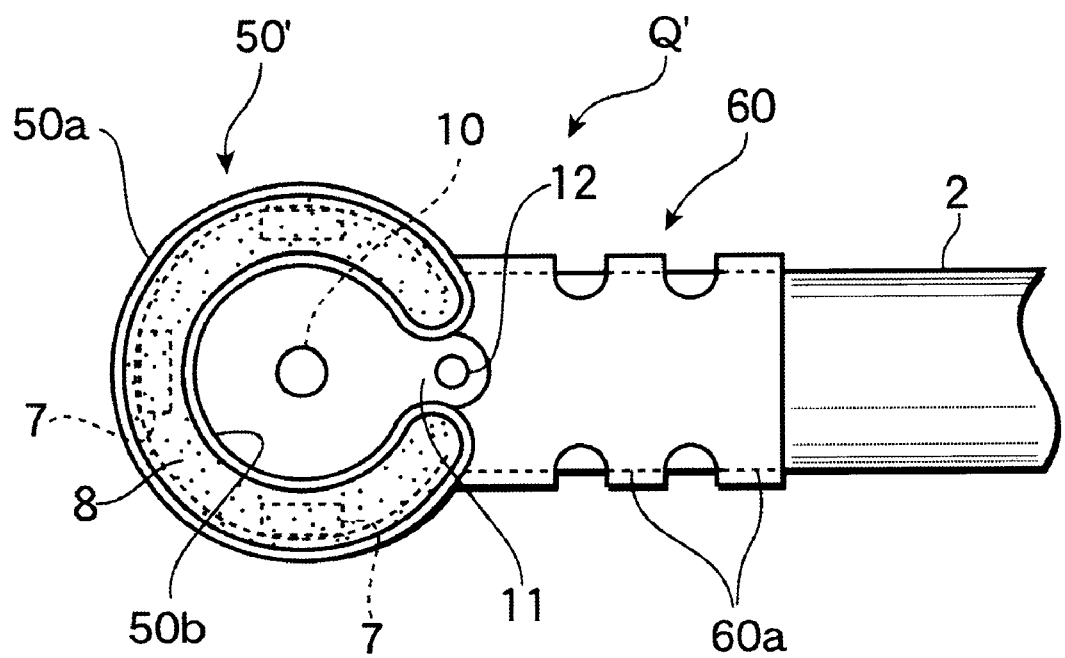
FIG. 8 is a bottom view of another embodiment of a lighting device according to the present invention.

FIG. 8 shows another embodiment of the lighting device of the present invention particularly suitable for use with a handpiece having an orifice 12 for injecting chip air and the like. In this embodiment, the lighting device Q' is similar to the lighting device Q, but has an LED holder 50' in the form of a horseshoe container having a space 11 between the two ends. LEDs 7 are arranged at regular 90° intervals in the LED holder 50'. When the lighting device Q' is mounted on a handpiece with the clip 60 engaging the transition portion as in the previous embodiment, the LED holder 50' can be placed on the lower side of the head 1 without blocking the orifice 12. The space 11 between the two ends of the holder 50' is placed over the orifice 12 to allow injection of chip air, washing water, and the like through the orifice 12 toward the treatment site, while the LEDs 7 are arranged around the tool 11 to illuminate the treatment site over a range as wide as 360° substantially without casting a shadow in treatment.

As in the previous embodiment, the LED holder 50' may also be filled with a transparent, heat resistant synthetic resin 8 to cover and protect the LEDs 7.

The lighting devices Q and Q' have been discussed as having the clip 60, but the clip 60 does not have to be provided. Only the LED holders 50 and 50' may be used as lighting devices, and may be fixedly or detachably mounted on a handpiece in a suitable manner.

The present invention has been discussed particularly with regard to the application to a contra-angle handpiece. However, those skilled in the art would appreciate that the present invention may also be applied as well to handpieces of straight and other types, and other dental or medical instruments such as air turbines, mirrors, ultrasonic scalers, air scalers, hand scalers, periodontal curets, vacuums, cylinders, and saliva ejectors. In that case, the lighting device of the present invention may be mounted on such instruments in any suitable manner as long as the LED holder is mounted on the distal part of the instrument and the LEDs are arranged so as to illuminate the treatment site substantially without casting a shadow on the site in treatment.

According to the present invention, the lighting device employs as light sources a plurality of LEDs, which consume only a small amount of electric power, so that a portable DC battery or a dry cell may be used as a power supply. Since such battery and cell are readily available and portable, the present invention provides a portable lighting device for use with a dental or medical instrument at low cost.

The LEDs are arranged so as to illuminate a treatment site substantially without casting a shadow on the site in treatment. Thus, effectiveness in treatment of a site may be improved. When the LEDs are arranged substantially around a tool in the distal part of a dental or medical instrument, a dark treatment site may be illuminated over a range as wide as 360° so that the effectiveness may further be improved.

The LEDs may be supplied with electric power from a power supply via flexible connecting means such as lead wires or flexible substrate, so that installation of the connecting means is facilitated even in a handpiece of a contra-angle type. Further, no problems such as cracking of optical fibers will occur unlike the conventional lighting device having a halogen lamp as a light source and an optical fiber as a light guide. Thus, the lighting device as well as the dental or medical instrument having such lighting device may be manufactured at low cost.

The LEDs disposed in the LED holder may be covered with a heat resistant synthetic resin, which protects the LEDs from damage due to heat experienced in autoclaving. Thus, the lighting device of the present invention may be sterilized by autoclaving readily and repeatedly without attenuation of light, and may be used for a prolonged period of time.

The lighting device of the present invention may be detachably mounted on a dental or medical instrument, and the dental or medical instrument of the present invention has the lighting device that may be made detachable. Thus, the lighting device may be easily detached from the instrument for sterilization, or easily exchanged when damaged. When the lighting device is provided with a clip, the detachment of the lighting device may further be facilitated.

Although the present invention has been described with reference to the preferred embodiment, it should be understood that various modifications and variations can be easily made by those skilled in the art, and any one or more of the features described herein may be combined as desired, without departing from the spirit of the invention. Accordingly, the foregoing disclosure should be interpreted as illustrative only and is not to be interpreted in a limiting sense. The present invention is limited only by the scope of the following claims.

What is claimed is:

1. A lighting device for use with a dental or medical instrument having a tool in a distal part of said instrument for treatment of a site, said lighting device comprising:
   a plurality of light emitting diodes, and
   an LED holder encasing said plurality of light emitting diodes and capable of being mounted on a distal part of said instrument,
   wherein said plurality of light emitting diodes are arranged so as to illuminate said site substantially without casting a shadow on said site in treatment when said LED holder is mounted on said instrument,
   wherein said light emitting diodes are covered with heat resistant material, and
   wherein said lighting device does not have optical fibers as a light guide.

2. The lighting device of claim 1, wherein said LED holder substantially has a shape selected from the group consisting of an annular shape and a horseshoe shape, and wherein said light emitting diodes are arranged so as to be disposed substantially around said tool when said LED holder is mounted on said instrument.

3. The lighting device of claim 2, wherein said light emitting diodes are arranged substantially at regular intervals.

4. The lighting device of claim 1, wherein said LED holder is capable of being fixedly mounted on said distal part of said instrument.

5. The lighting device of claim 1, wherein said LED holder is capable of being detachably mounted on said distal part of said instrument.

6. The lighting device of claim 5 further comprising a clip attached to said LED holder, said clip capable of detachably engaging with said instrument to detachably hold said LED holder with respect to said distal part of said instrument.

7. The lighting device of claim 6, wherein said clip is integrally formed with said LED holder.

8. A dental or medical instrument comprising:
   a tool in a distal part of said instrument for treatment of a site, and
   a lighting device comprising:
   a plurality of light emitting diodes, and
   an LED holder encasing said plurality of light emitting diodes and provided in said distal part of said instrument, wherein said plurality of light emitting diodes are arranged so as to illuminate said site substantially without casting a shadow on said site in treatment, wherein said plurality of light emitting diodes are covered with a heat resistant material, and wherein said lighting device does not have optical fibers as a light guide.

9. The instrument of claim 8, wherein said LED holder is integrally formed on said distal part of said instrument.

10. The instrument of claim 9, wherein said plurality of light emitting diodes are arranged substantially around said tool substantially in a shape selected from the group consisting of an annular shape and a horseshoe shape.

11. The instrument of claim 10, wherein said plurality of light emitting diodes are arranged substantially at regular intervals.

12. The instrument of claim 8, wherein said LED holder is fixedly mounted on said distal part of said instrument.

13. The instrument of claim 8, wherein said LED holder is detachably mounted on said distal part of said instrument.

14. The instrument of claim 13, wherein said lighting device further comprises a clip attached to said LED holder, said clip capable of detachably engaging with said instrument to detachably hold said LED holder with respect to said distal part of said instrument.

15. The instrument of claim 14, wherein said clip is integrally formed with said LED holder.

16. The instrument of claim 8, wherein said LED holder substantially has a shape selected from the group consisting of an annular shape and a horseshoe shape, and wherein said plurality of light emitting diodes are arranged substantially around said tool.

17. The instrument of claim 16, wherein said plurality of light emitting diodes are arranged substantially at regular intervals.

* * * * *